United States Patent
Redd et al.

(10) Patent No.: US 7,159,533 B1
(45) Date of Patent: Jan. 9, 2007

(54) SYSTEM AND METHOD FOR MONITORING THE DELIVERY OF GAS TO A PERSON'S AIRWAY

(76) Inventors: Iris Gail Redd, 10212 Pollard Creek Rd., Mechanicsville, VA (US) 23116; John Lawrence Redd, 10212 Pollard Creek Rd., Mechanicsville, VA (US) 23116

(*) Notice: Subject to any disclaimer, the term of this patent is extended or adjusted under 35 U.S.C. 154(b) by 484 days.

(21) Appl. No.: 10/243,318

(22) Filed: Sep. 12, 2002

(51) Int. Cl.
G01F 15/00 (2006.01)

(52) U.S. Cl. ............... 116/274; 116/112; 128/205.23; 222/40; 96/422

(58) Field of Classification Search ........ 116/276, 116/271, 273, 274, 266, 264, 112; 96/416, 96/417, 422; 55/DIG. 34; 222/40; 128/205.23, 128/205.15, 205.18
See application file for complete search history.

(56) References Cited

U.S. PATENT DOCUMENTS

| | | | | |
|---|---|---|---|---|
| 799,603 A | * | 9/1905 | King | ............... 116/274 |
| 1,783,379 A | * | 12/1930 | Jacob | ............... 116/274 |
| 1,783,644 A | * | 12/1930 | Geyer et al. | ............... 116/274 |
| 3,744,236 A | * | 7/1973 | Kishida | ............... 368/226 |
| 4,098,271 A | | 7/1978 | Maddock | |
| 4,188,946 A | | 2/1980 | Watson et al. | |
| 4,745,877 A | | 5/1988 | Chang | |
| 4,790,832 A | * | 12/1988 | Lopez | ............... 604/283 |
| 5,092,809 A | * | 3/1992 | Kessler | ............... 446/217 |
| 5,293,864 A | * | 3/1994 | McFadden | ............ 128/201.29 |
| 5,320,092 A | * | 6/1994 | Ryder | ............ 128/202.22 |
| D348,753 S | * | 7/1994 | Stojanovski | ............... D30/106 |
| 5,374,239 A | * | 12/1994 | Mischenko | ............... 604/8 |
| 5,937,852 A | * | 8/1999 | Butler et al. | ............ 128/203.12 |
| 5,944,054 A | * | 8/1999 | Saieva | ............ 137/625.4 |
| 5,979,442 A | * | 11/1999 | Orr | ............ 128/204.18 |
| 6,073,628 A | * | 6/2000 | Butler et al. | ............ 128/203.12 |
| 6,386,196 B1 | | 5/2002 | Culton | |
| 6,578,571 B1 | * | 6/2003 | Watt | ............ 128/200.14 |

* cited by examiner

*Primary Examiner*—Diego Gutierrez
*Assistant Examiner*—Tania C. Courson
(74) *Attorney, Agent, or Firm*—Denis R. O'Brien

(57) ABSTRACT

A gas delivery system and method are disclosed in which a flow indicator is interposed between the distal end of a conduit connected to a gas source and a device for introducing the gas in the airway of an individual so that the individual, or some other person in visual contact with the individual, can easily determine whether or not gas is flowing through the system.

4 Claims, 3 Drawing Sheets

SYSTEM AND METHOD FOR MONITORING THE DELIVERY OF GAS TO A PERSON'S AIRWAY

BACKGROUND OF THE INVENTION

1. Field of the Invention

The present invention relates generally to systems that deliver breathing gases to individuals in need thereof, particularly within a medical context, although other contexts are recognized such as oxygen delivery systems used in high altitude flying.

2. Description of the Prior Art

A very common medical situation is one in which it is necessary to deliver a gas from a gas source to an individual's airway, and, consequently, a large variety of gas delivery systems have been designed for this purpose. Although the prior art of such gas delivery systems is far too copious to inventory here, a representative example may be found in U.S. Pat. No. 4,188,946 to Watson and Rayburn.

Such gas delivery systems comprise at least three necessary elements: 1) a source of the desired gas; 2) a conduit for transmitting the gas from the source to the individual receiving the gas; and, 3) a device for introducing the gas to the airway of the individual. The terms "proximal" and "distal" are used herein in reference to the source; i.e., "proximal" means towards or near the source and "distal" means away from the source; i.e., toward or near the individual receiving the gas.

The source of the gas is normally a tank containing the gas under pressure, or a pump that pumps the gas directly into the system. For the purposes of this invention, a gas outlet built into a wall or bulkhead may also be considered a source. The gas to be delivered is usually oxygen, either alone or admixed with other gases and/or pharmacological agents. A flow-regulator is often provided to control the flow rate of the gas. In some circumstances a demand-valve limits the flow of gas to just the inspiration phase of the person's respiratory cycle; in other circumstances the gas flows freely.

Flexible tubing is generally used as conduits in gas delivery systems, particularly in the distal end of the system. Such tubing is often transparent and made of an elastic material. Depending on the application, the tubing may have an internal diameter ranging from a few millimeters to a few centimeters.

The device for introducing the gas to the individual's airway takes one of a number of forms. One is simply a mask that connects to the distal end of the conduit and covers the individual's nose and mouth simultaneously such that substantially all of the gas entering the individual's airway is that which is delivered by the system. Another device for introducing the gas to the individual's airway is an endotracheal tube, which allows delivery of the gas directly into the trachea of an individual. In other situations it is sufficient to employ a nasal cannula. This is normally a hollow, gas-conducting device having an inlet and two outlets. The inlet of the cannula is attached to the distal end of the conduit and the outlets are placed below the individual's nose such that each of the two outlets is adjacent one of the nares. As long as gas is flowing through the system, the individual inhales an unspecified mixture of the delivered gas and ambient air. If the flow of the gas through the system is cut off, the individual inhales only ambient air, which may not have a sufficiently high oxygen content to sustain the individual.

A means to detect whether or not gas is flowing through the system is an element of existing gas delivery systems that is often critical to the proper operation of the system. Flow-meters and flow-indicators are two means employed to determine whether gas is flowing through a gas delivery system. The standard flow-meter used in medical situations is one that is attached at or near the source of the gas and provides a hollow tube containing a ball in the lumen thereof. The lumen of the tube is in communication with the lumen of the conduit so that gas flowing through the system causes the ball to rise in the tube. The height to which the ball rises in the tube is directionally proportional to the flow rate of the gas. In hospital settings such flow meters are normally attached to a wall behind the individual receiving the gas. In most instances the flow-meter is combined with a flow-valve.

Flow indicators are devices used to visually detect the flow of fluids through conduits without necessarily measuring the rate of flow. A common type of flow indicator is a rotary sight flow indicator, which comprises a rotatable member positioned in a chamber that is in communication with the conduit. The rotatable member is visible through a window in the chamber. When fluid moves through the chamber, it causes the rotatable member to rotate, and this provides a visible indication that the fluid is moving. A representative rotary sight flow indicator is disclosed by U.S. Pat. No. 4,745,877 to Chang.

Such flow indicators are used in gas delivery systems. For instance, U.S. Pat. No. 6,386,196 to Culton discloses a rotary sight flow indicator combined with a flow meter connected to a gas source. Culton also provides a very useful whistle element that gives an audible warning if the conduit should slip off of the flow-indicator while gas is running through it.

SUMMARY OF THE INVENTION

1. Shortcomings of Prior Art Overcome by the Invention

In situations where gas delivery systems are employed to deliver gases to individuals who require the gases to breathe, failure of the system can cause catastrophic results. In recognition of this obvious point the prior art discloses various types of flow-meters and flow indicators, as discussed above. These prior art devices, however, are positioned proximally in the system; i.e., at or near the source of the gas.

Proximal placement of a flow-indicator presents at least two potentially dangerous problems that are overcome by the present invention. The first is that the flow indicator can be virtually hidden from the individual for whom the gas is intended. The Culton flow-indicator is a good example of a flow-indicator being associated with a flow-valve located on a wall, often somewhere behind the patient and occluded by hanging drapes or other obstructions. Another common situation is one in which the flow indicator is connected to a portable gas tank or pump. Such tanks and pumps are often kept out of the way by placing them on the floor, under the bed, or behind furniture or other obstructions.

Such flow indicators are not easily observable by the person receiving the gas because those who are in need of breathing gases normally do not have the strength or agility to twist around to locate concealed flow indicators. Because the individual cannot see the flow-indicator, if gas flow is interrupted, the individual may not know it, particularly if the individual is severely debilitated and a nasal cannula is in use. Other persons in the vicinity of the individual also may have no indication that the gas flow has been interrupted because often they, too, cannot see the concealed flow indicator. What is required is an improved gas delivery system having a flow indicator adjacent to the individual receiving the gas so that the individual receiving the gas can easily and conveniently see the flow indicator and determine whether gas is flowing through the system.

A second potentially dangerous problem that is overcome by the present invention is that the proximally-placed flow indicators are too far "upstream" from the delivery point; i.e. the individual receiving the gas. In the hospital setting the length of tubing between the flow-indicator and the individual may be three meters or more. If the tubing develops a leak or is disconnected at some point between the flow-indicator and individual, a proximally-placed flow-indicator will show that the system is operating normally when, in fact, the individual is not receiving any gas at all. What is required is an improved gas delivery system having a flow indicator distally-placed at or near the individual receiving the gas so that all interruptions of flow in the system, no matter how far upstream, are easily detected.

A third problem with the prior art that is overcome by the present invention is that the rotary sight flow indicators of the prior art are designed such that should the rotatable member become stuck and unable to move, the gas will not be able to flow through the flow indicator, and, consequently, gas flow to the individual will cease. What is required is an improved gas delivery system having a rotary sight flow indicator of a type that will allow gas to flow through it even if the rotatable member is stuck and unable to rotate.

A fourth problem with the prior art that is overcome by the present invention is that the flow indicators cannot be easily retrofit into existing systems. For instance, the indicator claimed by Culton, supra, requires a plurality of metal fittings so that it can be attached to existing flow meters. What is required is a flow indicator that can be easily retrofit into existing gas delivery systems without the necessity of providing fittings, clamps, or other hardware.

A fifth problem of the prior art that is overcome by the present invention is that the complexity of the prior art requires excessive manufacturing costs which mitigate against wide-spread use and acceptance of the prior art flow indicators. What is required is a flow indicator that is simple, elegant, and inexpensively made that can be widely used to improve gas delivery systems.

A sixth problem with the prior art that is overcome by the present invention is that the prior art flow indicators include metal fittings and other heavy components that make the flow indicators too heavy to be conveniently used as a personal flow indicator at the distal end of the conduit adjacent to the individual receiving the gas. For instance, a flow indicator of the type described by Culton, supra, used in conjunction with a nasal cannula and positioned adjacent the individual receiving the gas is so heavy that it would pull the cannula off the individual's face, thereby defeating the purpose of the gas delivery system. What is required is an improved gas delivery system having a flow indicator that is sufficiently light that it can be incorporated into the distal portion of the conduit adjacent the individual receiving the gas without defeating or being antagonistic to the purpose of the gas delivery system.

2. Objects of the Invention

The invention solves the foregoing shortcomings of the prior art by achieving the following objects:

A first object of the invention is to provide a flow indicator positioned at the distal end of the conduit of a gas delivery system near to, and within easy sight of, the individual to whom the gas is being delivered;

A second object of the invention is to provide a gas flow indicator that can be easily observed by the individual to whom the gas is being delivered, as well as by other persons in the vicinity of the individual to whom the gas is being delivered;

A third object of the invention is to provide a gas flow indicator that can be easily retrofit into exiting gas delivery systems;

A fourth object of the invention is to provide a gas flow indicator that is inexpensively produced and can therefore be made widely accessible;

A fifth object of the invention is to provide a gas flow indicator that is designed and constructed in a manner in which gas will continue to flow through the system even if the flow indicator is, or becomes, defective.

A sixth object of the invention is to provide a gas flow indicator that is light enough to be incorporated into the distal end of the conduit of a gas delivery system adjacent the individual receiving the gas without inconvenience or discomfort to the individual and without defeating the purpose of the gas delivery system.

BRIEF DESCRIPTION OF THE FIGURES

The above and other objects, features and advantages of the invention will become apparent from a consideration of the following description and the accompanying figures, in which.

DETAILED DESCRIPTION OF THE INVENTION
TABLE OF FIG. REFERENCE NUMBERS

| 100 | housing | 110 | transparent surface |
| 120 | inlet port | 130 | outlet port |
| 140 | rotatable member | 150 | axle |
| 160 | 1$^{st}$ stationary crosspiece | 170 | 2$^{nd}$ stationary crosspiece |
| 310 | paddle wheel | 320 | impellers |
| 330 | first disc | 332 | second disc |
| 338 | lower transparent housing | 340 | upper transparent housing |
| 350 | inlet port | 360 | outlet port |
| 380 | axle | 410 | nasal cannula |
| 420 | cannula outlet ports | 470 | conduit |
| 474 | conduit distal end | 476 | conduit proximal end |
| 480 | individual | 486 | gas source |

DETAILED DESCRIPTION

Figure 1:
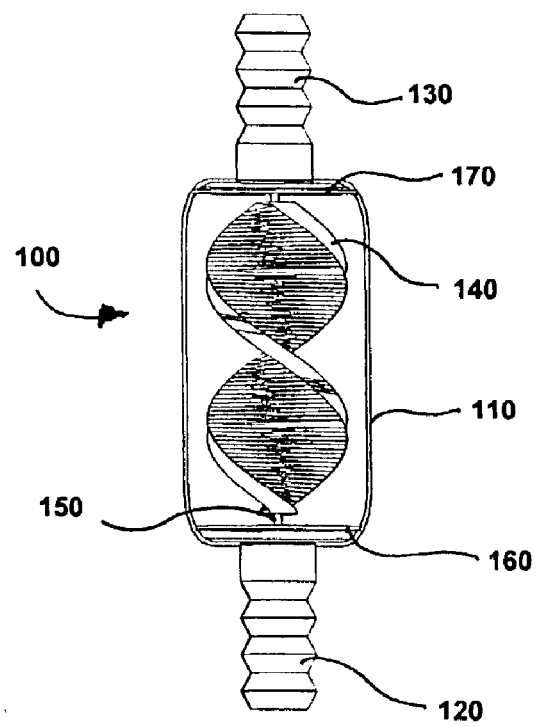
FIG. 1. shows ah embodiment of the invention that employs a helical rotatable member.

FIG. 1 shows a preferred embodiment of the invention comprising a flow indicator in which a helix is employed as a rotatable member to indicate the flow of gas through a gas delivery system.

The flow indicator has a housing 100 that forms a chamber through which the gas flows. The housing has at least one transparent surface 110 so that the interior chamber formed by the housing can be viewed from without the flow indicator. In the present embodiment the housing is cylindrical with the side of the cylinder comprising a single transparent surface, thus providing a 360° view into the chamber.

The housing has an inlet (proximal) end and an outlet (distal) end. The housing includes at least one inlet port 120 in the proximal end and at least one outlet port 130 in the distal end. Both ports may be located substantially concentrically with respect to the housing, or one or both ports may be offset from the centerline of the housing in order to effectuate more efficient flow of gas, depending on the type of rotatable member employed and the geometrical shape of the housing. The embodiment of FIG. 1 shows concentrically located inlet and outlet ports. The inlet and outlet ports communicate with the chamber of the housing so that gas flowing through the inlet port passes through the chamber and out the outlet port.

Figure 4:
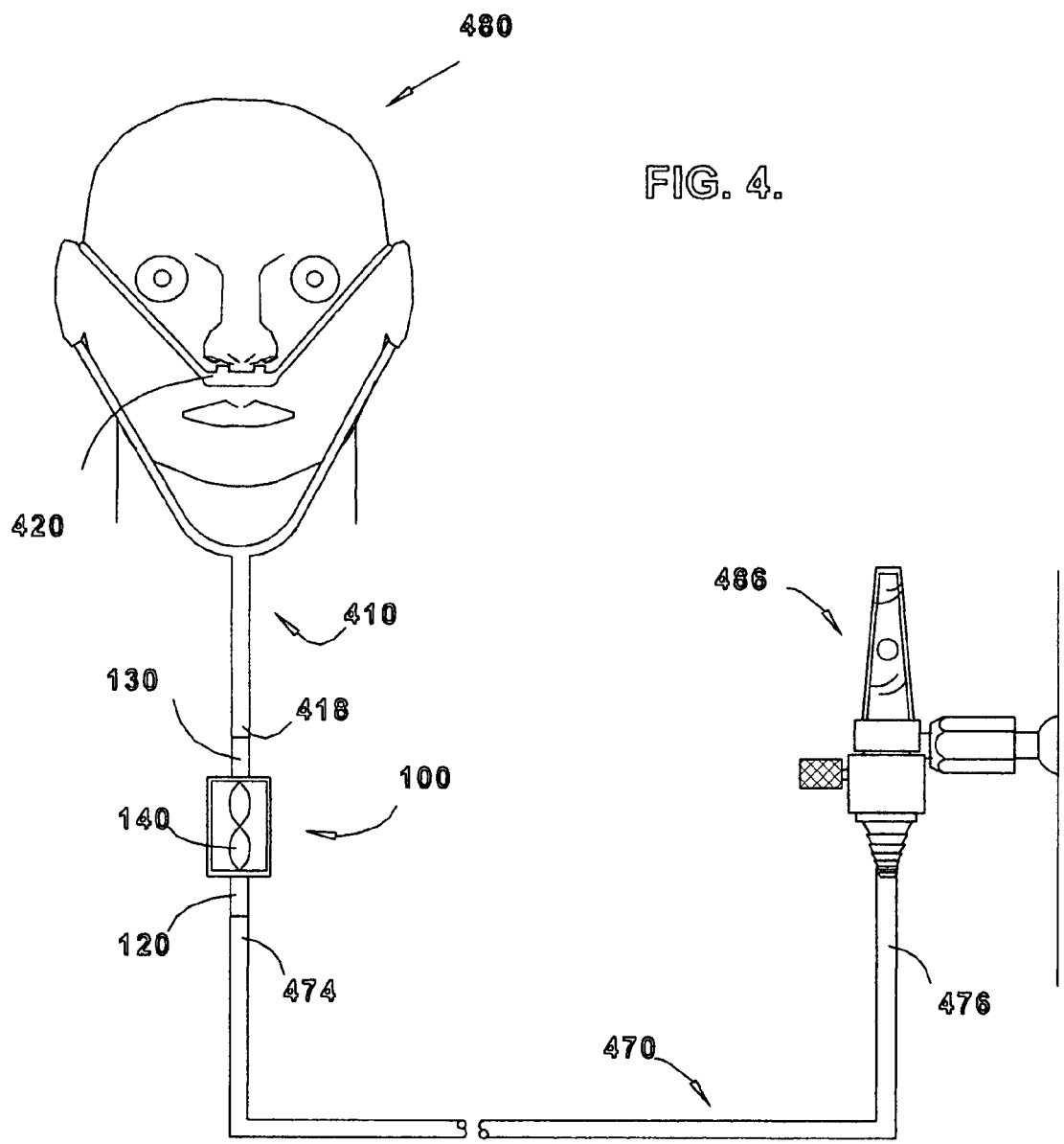
FIG. 4. is a diagram representing the gas delivery system disclosed herein.

The conduit of the gas delivery system may be considered as two sections with respect to the flow indicator. The proximal conduit (not shown) connects the inlet port 120 to the source (not shown), and the distal conduit (not shown) connects the outlet port 130 to the device for introducing the gas into the airway of the individual. Alternatively, the device for introducing gas into the airway of the individual may connect directly to the outlet port, thereby dispensing with the distal conduit, as illustrated in FIG. 4.

The embodiment shown in FIG. 1 includes a means of retrofitting the invention to an existing gas delivery system. The diameter of the inlet and outlet ports are approximately equal to the diameter of the conduit. Having cut the conduit at a position near the individual receiving the gas, the cut ends of the conduit are then frictionally fayed to the inlet and outlet ports. With the gas delivery system's conduit thus in communication with the inlet port and the outlet port, the system is sealed such that gas entering the device through the inlet port passes through the chamber of the housing and exits the outlet port without loss of gas from the delivery system. From the present disclosure, other functionally equivalent means of retrofitting the invention to existing gas delivery systems will be obvious to those skilled in the art.

A rotatable member 140 for producing a visible signal indicating the flow of gas through the housing is enclosed within housing 100 and is visible from without the housing through the transparent surface 110 of the housing. The rotatable member has at least one surface upon which gas passing through the chamber impinges. In the preferred embodiment the rotatable member is in the form of a helix comprising a first surface and second surface twisted about its axis of rotation. As can be seen in FIG. 1, the width of the helix at its widest dimension is smaller than the diameter of the housing, thereby allowing free rotation of the helix within the chamber of the housing.

An axle 150 runs through the helix, coincident with its axis of rotation so that the helix rotates freely about the axle. One end of the axle is attached to a first stationary crosspiece 160 affixed at the proximal (inlet) end of the housing, and the other end of the axle is attached to a second stationary crosspiece 170 affixed at the distal (outlet) end of the housing. These crosspieces are more easily seen in FIG. 2. which shows the invention in perspective view with a portion of the transparent surface of the housing removed for purposes of facilitating comprehension of the invention. The aforementioned crosspieces are fixedly attached to the housing adjacent the inlet port and outlet port, respectively. The crosspieces have a circular outer edge with a diameter that is substantially the same as the internal diameter of the housing. They are affixed to the housing by an appropriate adhesive means, such as glue, resin, chemical welding, or other functionally equivalent means. The crosspieces are constructed so as to 1) have a minimum effect on restricting the flow rate of gas through the chamber, and 2) direct the flow of gas through the chamber in a way that maximizes the force of the gas on the rotatable member.

The ends of the axle 150 are inserted into indentations, or holes, or their functional equivalents in the crosspieces, thereby orienting the axle and rotatable member substantially parallel to the flow of the gas through the chamber. The diameter of the indentations or holes are sufficiently larger than the diameter of the axle to allow free rotation of the axle within the indentations or holes.

By employing a helix as a rotatable member, the orientation of the axle with respect to the flow of gas is not critical. For example, an alternative orientation of the helix is with its axle substantially normal to the flow of gas through the housing. To accommodate this orientation, the shape of the housing could be spherical, and the crosspieces dispensed with.

Given the arrangement of the constituent elements of the embodiment herein disclosed, it can be appreciated that as long as gas is entering the inlet port 120 and exiting the outlet port 130, the rotatable helix 140 will rotate freely about its axle 150 because the moving gas impinges upon the surfaces of the helix and causes the helix to rotate. Conversely, when gas stops flowing through the flow indicator, the helix stops rotating, there no longer being a force necessary for inducing rotation of the helix. The rotating helix thus becomes a visual signal indicating that gas is flowing through the gas delivery system. With the flow indicator located at the distal end of the gas delivery system adjacent the individual to whom the gas is delivered, the individual can easily visually confirm that the system is working by determining whether the helix is rotating. Likewise, any persons in the vicinity of the individual receiving the gas can also tell immediately if the gas is flowing because the flow indicator is positioned within a few inches of the individual's face. It is not necessary to search behind drapes or other obstructions to find a flow-indicator attached to the wall or to try and locate a flow indicator attached to a tank that is hidden beneath a bed or behind a chair.

It would be useful to amplify or enhance the visual signal produced by the rotatable member when gas is flowing through the flow indicator. Many ways can be anticipated. For instance, the rotatable member can be colored with an attention-attracting color-scheme such as using a combination of colors that produce the optical illusion of turning into a completely distinct color when the helix is rotating. For example, one surface of the helix can be blue and the other surface yellow, such that when the helix rotates at a rotational speed higher than the flicker-rate of the human visual system, the helix appears as green. In addition, if at least one surface of the helix is coated with discontinuous bands of luminescent material, or if an edge is coated with luminescent material, rotation of the helix in the dark will be evident due to the illusion of a solid surface of luminescence during rotation, whereas the stationary helix will appear in the dark as discontinuous bands or a single line of luminescence, respectively.

Figure 2:
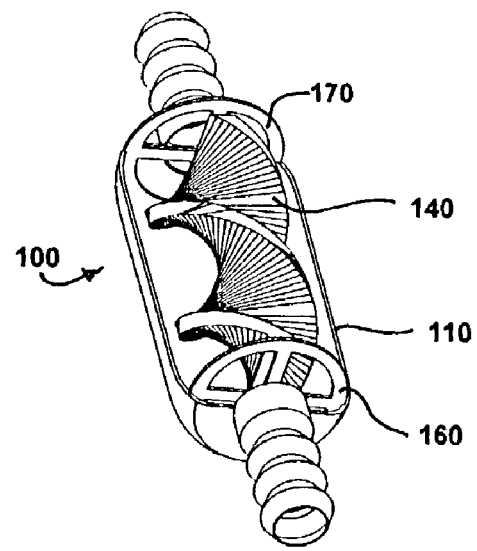
FIG. 2. is a perspective view of the embodiment shown in FIG. 1. with part of the transparent surface removed.

In contemplating FIG. 2. the primary advantage of an helical rotatable member becomes evident: Should the helix become stuck and unable to rotate for any reason, the gas will nevertheless continue to flow through the housing.

Although the best mode known to us is that in which a helix is used as the rotatable member, it is anticipated that the rotatable member may assume any shape or form that can be caused to rotate in the presence of a flowing gas.

Figure 3:
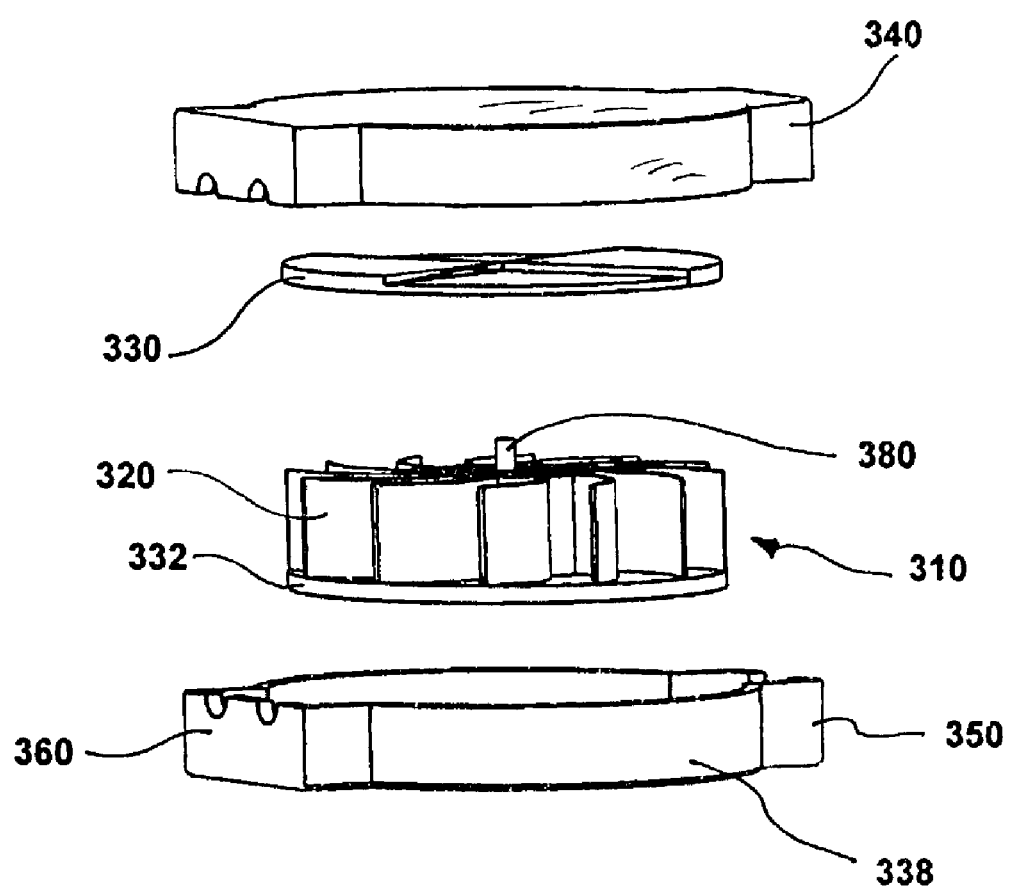
FIG. 3. is an exploded, perspective view of an embodiment of the present invention employing a paddle-wheel type rotatable member.

Likewise, while the form of the housing disclosed above is that of an elongate cylinder, other forms are anticipated that will accommodate various types of rotatable members. For example, FIG. 3 shows an alternative embodiment in which the rotatable member is a paddle-wheel 310 having a plurality of impellers 320 radiating from an axle 380. These impellers provide a surface upon which flowing gas impinges. In the present example, the impellers are sandwiched between a first disc 330 and a second disc 332, the discs being oriented parallel to one another and concentrically oriented with the paddle-wheel and in communication with the impellers such that when the impellers rotate, the discs rotate also.

The paddle-wheel is housed in a chamber produced by a lower transparent housing 338 and an upper transparent housing 340, which form a compressed cylinder with an internal diameter sufficiently larger than the diameter of the paddle-wheel to allow for the free rotation of the paddle-wheel within the chamber. Because the housing is transparent, the outer surfaces of the discs are visible from without the housing.

The axle 380 of the paddle-wheel is oriented normal to the flow of gas through the housing. Consequently, gas passing through the chamber impinges upon the impellers of the paddle-wheel, causing it to rotate. The discs can be seen rotating through the transparent housing, thus providing a visual signal that gas is flowing through the system.

In embodiments of the invention such as the paddle-wheel in which the axle is oriented substantially normal to the flow of gas, a variety of means for mounting the rotatable member are anticipated. For example, ends of the axle can be mounted directly into indentations provided in the housing wall and the crosspieces of the helix embodiment, above, can be dispensed with.

The visual signal produced by the rotating paddle-wheel can be amplified by the techniques disclosed above with reference to the helical rotatable member. For instance, by coating adjacent areas on each disc with yellow and blue colors, the rotating paddle-wheel appears to be green when rotating and yellow/blue when stationary; green therefor indicates the flow of gas. Also, the discs can be dispensed with altogether and the impellers coated so as to amplify the visual signal.

FIG. 4. shows the flow indicator 100 of the present invention used in conjunction with a nasal cannula 410. FIG. 4. shows the gas delivery system of the present invention and emphasizes the placement of the flow indicator at the distal end 474 of the conduit 470 so that the flow indicator is sufficiently close to the individual to allow the individual easily to observe movement of the rotatable member and thereby determine whether gas is flowing through the system.

The standard nasal cannula most commonly in use consists of tubing that bifurcates into two branches leading to a nose-piece with two outlet ports 420. The outlet ports are placed adjacent to the nares of the individual 480 receiving the gas so that gas flows out of the outlet ports and directly into the airway of the individual. The cannula is held in place by being looped over the individual's ears, or by means of an elastic strap, or by other means not pertinent to the present invention.

The preferred flow indicator is substantially transparent, as noted above, and made of a lightweight material such as plastic, polycarbonate, or polypropylene so that it is light enough to hang from the cannula without causing discomfort and without pulling the outlet ports away from the individual's nose. From the present disclosure, appropriate and suitable materials of construction will be obvious to those skilled in the art. The inlet port 120 of the flow indicator is connected to the distal end 474 of conduit 470, which leads proximally to the gas source 486. The outlet port 130 of the flow-indicator is connected to the nasal cannula just upstream of the bifurcation. Consequently, gas flows from the source through the conduit, into the flow-indicator and out of the flow-indicator into the nasal cannula, which directs the gas through the outlet ports to the airway of the individual receiving the gas. Gas flowing through the flow indicator causes the rotatable helix 140 to rotate, thereby producing a visual signal that the gas is flowing.

Thus positioned in the distal end of the gas delivery system, the flow indicator can be easily observed by the individual receiving the gas and by any caretakers or other persons who have visual contact with the individual receiving the gas.

From FIG. 1. taken in conjunction with FIG. 4. it will be obvious that the flow indicator of the present invention can be retrofit into the distal end of an existing gas delivery system. One means of accomplishing this is that the inlet port 120 and the outlet port 130 of the embodiment shown in FIG. 1. and FIG. 2. have diameters substantially equal to the diameter of the conduit and nasal cannula, respectively. Consequently, the conduit and cannula can be frictionally fayed to the inlet and outlet ports, thereby providing a leak-proof seal.

By interposing the flow indicator between two cut ends of the conduit in the distal end of the system, or between the distal end of the conduit and the nasal cannula, the benefits of the invention can be easily achieved.

SUMMARY OF THE INVENTION

The foregoing discloses a novel and useful improvement to a gas delivery system in which a gas flow indicator is integrated into the distal end of the system to make it easier for the individual receiving the gas, as well as other persons nearby, to determine whether or not gas is flowing through the system. The embodiments disclosed herein are not meant to be exclusive of other ways of making and practicing the invention. Upon consideration of the disclosures and claims, many equivalent means of making and practicing the invention will become evident to those skilled in the art. It is understood that the present invention is not limited to the embodiments disclosed above but encompasses any and all embodiments within the scope of the following claims.

We claim:

1. An improved gas delivery system of the type used to deliver gas to the airway of an individual, the improvement comprising a flow indicator incorporated into the gas delivery system sufficiently close to the individual to allow the individual easily to observe said flow indicator and thereby determine whether gas is flowing through the system, wherein said flow indicator includes:
   a) a housing that forms a chamber through which the gas flows, said housing having at least one transparent surface;
   b) at least one inlet port;
   c) at least one outlet port; and
   d) at least one rotatable member mounted within said housing and visible from without said housing through said transparent surface, said rotatable member having:
      i) an axis of rotation;
      ii) at least one surface upon which the gas flowing through the flow indicator impinges; and, iii) an axle, said axle being substantially coincident with said axis of rotation; and, e) means for mounting said rotatable member within said housing such that said rotatable member rotates freely about said axle when the gas is flowing through the chamber, thereby producing a visible signal indicating the flow of gas through the chamber, said means for mounting the rotatable member having i) a first stationary crosspiece affixed to said housing adjacent said inlet port; and, ii) a second stationary crosspiece affixed to said housing adjacent said outlet port, said axle being rotatably mounted to said first crosspiece and said second crosspiece, said axle thereby oriented substantially parallel to the flow of gas through said housing such that said rotatable member rotates about said axle when gas passing through said chamber impinges on the surface of said rotatable member.

2. A gas delivery system as recited in claim 1, wherein the rotatable member is a helix.

3. A gas delivery system for delivering gas to a person's airway, comprising:

a) a gas source;

b) a device for introducing the gas into the person's airway, the device having at least one inlet for receiving the gas and at least one outlet through which the gas passes from the device to the person's airway;

c) a conduit means for transmitting the gas from said gas source to said device for introducing the gas to the person's airway, said conduit means having a proximal end connected to said gas source, and a distal end;

d) a flow indicator means for determining whether the gas is flowing through the system, said flow indicator means interposed between said distal end of said conduit means and said inlet of said device for introducing the gas to the person's airway;

e) a housing that forms a chamber through which the gas flows, said housing having at least one transparent surface;

f) at least one inlet port connected to said distal end of said conduit means;

g) at least one outlet port connected to said inlet of said device for introducing the gas into the person's airway;

h) at least one rotatable member mounted within said housing and visible from without said housing through said transparent surface, said rotatable member having 1) an axis of rotation, 2) at least one surface upon which the gas flowing through the flow indicator impinges, and 3) an axle, said axle being substantially coincident with said axis of rotation;

i) means for mounting said rotatable member within said housing such that said rotatable member rotates freely about said axle when the gas is flowing through the chamber, thereby producing a visible signal indicating the flow of gas through the system;

j) a first stationary crosspiece affixed to the housing adjacent said inlet port; and k) a second stationary crosspiece affixed to the housing adjacent said outlet port, said axle being rotatably mounted to said first crosspiece and said second crosspiece, said axle thereby being oriented substantially parallel to the flow of gas through said housing such that said rotatable member rotates about said axle when gas passing through said chamber impinges on the surface of said rotatable member.

4. A gas delivery system as recited in claim 3, wherein said rotatable member is a helix.

* * * * *